United States Patent
Perez-Cruet et al.

(10) Patent No.: US 7,824,427 B2
(45) Date of Patent: Nov. 2, 2010

(54) MINIMALLY INVASIVE INTERBODY DEVICE

(76) Inventors: Miquelangelo J. Perez-Cruet, 1070 Timberlake Dr., Bloomfield, MI (US) 48302; John R. Pepper, 224 Beacon Hill Dr., Cheshire, CT (US) 06410; John A. Miller, 600 Waddington, Bloomfield Village, MI (US) 48301

( * ) Notice: Subject to any disclaimer, the term of this patent is extended or adjusted under 35 U.S.C. 154(b) by 64 days.

(21) Appl. No.: 11/623,356

(22) Filed: Jan. 16, 2007

(65) Prior Publication Data

US 2008/0172127 A1    Jul. 17, 2008

(51) Int. Cl.
*A61B 17/70* (2006.01)

(52) U.S. Cl. .................... 606/246; 606/249; 623/17.11; 623/17.16

(58) Field of Classification Search .................. 606/61, 606/60, 246, 249, 279, 108; 623/17.11–17.16
See application file for complete search history.

(56) References Cited

U.S. PATENT DOCUMENTS

| | | | |
|---|---|---|---|
| 4,232,670 A | | 11/1980 | Richter et al. |
| 4,625,722 A | | 12/1986 | Murray |
| 4,735,346 A | | 4/1988 | Stoody |
| 4,834,757 A | | 5/1989 | Brantigan |
| 4,878,915 A | * | 11/1989 | Brantigan ................. 623/17.11 |
| 5,159,732 A | | 11/1992 | Burke |
| 5,425,772 A | * | 6/1995 | Brantigan ................. 623/17.11 |
| 5,443,514 A | | 8/1995 | Steffee |
| 5,458,638 A | | 10/1995 | Kuslich et al. |
| 5,549,679 A | * | 8/1996 | Kuslich ..................... 623/17.12 |
| 5,569,262 A | | 10/1996 | Carney |
| 5,607,424 A | * | 3/1997 | Tropiano .................. 623/17.16 |
| 5,683,463 A | * | 11/1997 | Godefroy et al. ......... 623/17.16 |
| 5,716,415 A | | 2/1998 | Steffee |
| 5,788,702 A | | 8/1998 | Draenert |
| 5,885,292 A | | 3/1999 | Moskovitz et al. |
| 5,888,228 A | * | 3/1999 | Knothe et al. ............. 623/17.16 |
| 5,893,890 A | | 4/1999 | Pisharodi |

(Continued)

FOREIGN PATENT DOCUMENTS

JP    3091694 A    4/1991

(Continued)

OTHER PUBLICATIONS

Synthes Spine, Vertebral Spacer—AR, 2 pgs., Internet article.

*Primary Examiner*—Eduardo C Robert
*Assistant Examiner*—Christina Negrelli

(57) ABSTRACT

An interbody device that restores the disc space height between two vertebrae during spinal fusion surgery. The device includes a center plate surrounded by a perimeter portion that combine to have a relatively flat configuration in one dimension and relatively wide configuration in a perpendicular dimension. After the disc space has been cleared, the device is inserted into the disc space in a direction so that the wide dimension of the device is substantially parallel to the body of the vertebrae. The device is then rotated so that the wide dimension of the device becomes perpendicular to the vertebral body so as to cause the disc space height to be restored. Bone graft material is then introduced through a fill tube coupled to the device so that the bone graft material is distributed on both sides of the center plate and into the disc space.

15 Claims, 5 Drawing Sheets

U.S. PATENT DOCUMENTS

| | | | |
|---|---|---|---|
| 5,954,728 A | 9/1999 | Heller et al. | |
| 5,980,522 A * | 11/1999 | Koros et al. | 623/17.11 |
| 6,004,326 A | 12/1999 | Castro et al. | |
| 6,019,765 A | 2/2000 | Thornhill et al. | |
| 6,059,829 A | 5/2000 | Schlapfer et al. | |
| 6,066,174 A | 5/2000 | Farris | |
| 6,066,175 A | 5/2000 | Henderson et al. | |
| 6,080,158 A | 6/2000 | Lin | |
| 6,245,108 B1 | 6/2001 | Biscup | |
| 6,290,724 B1 | 9/2001 | Marino | |
| 6,309,421 B1 | 10/2001 | Pisharodi | |
| 6,375,655 B1 | 4/2002 | Zdeblick et al. | |
| 6,413,278 B1 | 7/2002 | Marchosky | |
| 6,425,920 B1 | 7/2002 | Hamada | |
| 6,471,724 B2 | 10/2002 | Zdeblick et al. | |
| 6,558,424 B2 * | 5/2003 | Thalgott | 623/17.16 |
| 6,610,065 B1 | 8/2003 | Branch et al. | |
| 6,709,458 B2 | 3/2004 | Michelson | |
| 6,716,245 B2 * | 4/2004 | Pasquet et al. | 623/17.11 |
| 6,746,454 B2 | 6/2004 | Winterbottom et al. | |
| 6,746,484 B1 | 6/2004 | Liu et al. | |
| 6,749,595 B1 | 6/2004 | Murphy | |
| 6,827,740 B1 | 12/2004 | Michelson | |
| 6,887,248 B2 | 5/2005 | McKinley et al. | |
| 6,942,698 B1 | 9/2005 | Jackson | |
| 6,976,949 B2 | 12/2005 | Winkler et al. | |
| 7,018,416 B2 | 3/2006 | Hanson et al. | |
| 7,025,771 B2 | 4/2006 | Kuslich et al. | |
| 7,048,743 B2 | 5/2006 | Miller et al. | |
| 7,118,579 B2 | 10/2006 | Michelson | |
| 7,125,425 B2 | 10/2006 | Foley et al. | |
| 7,128,760 B2 | 10/2006 | Michelson | |
| 7,156,877 B2 * | 1/2007 | Lotz et al. | 623/17.16 |
| 7,169,183 B2 | 1/2007 | Liu et al. | |
| 7,195,643 B2 * | 3/2007 | Jackson | 623/17.11 |
| 7,217,293 B2 | 5/2007 | Branch, Jr. | |
| 7,220,280 B2 | 5/2007 | Kast et al. | |
| 7,232,463 B2 | 6/2007 | Falahee | |
| 7,238,186 B2 | 7/2007 | Zdeblick et al. | |
| 7,306,611 B2 | 12/2007 | Cirotteau et al. | |
| 7,331,996 B2 | 2/2008 | Sato et al. | |
| 7,341,600 B2 * | 3/2008 | Lange et al. | 623/17.11 |
| 7,351,244 B2 | 4/2008 | Hamada | |
| 7,371,241 B2 | 5/2008 | Evans et al. | |
| 7,381,178 B2 | 6/2008 | Winkler et al. | |
| 7,473,256 B2 | 1/2009 | Assell et al. | |
| 7,479,160 B2 | 1/2009 | Branch et al. | |
| 7,569,074 B2 | 8/2009 | Eisermann et al. | |
| 7,572,263 B2 | 8/2009 | Preissman | |
| 7,655,027 B2 | 2/2010 | Michelson | |
| 2001/0010021 A1 * | 7/2001 | Boyd et al. | 623/17.11 |
| 2002/0143401 A1 | 10/2002 | Michelson | |
| 2002/0177897 A1 | 11/2002 | Michelson | |
| 2004/0030387 A1 * | 2/2004 | Landry et al. | 623/16.11 |
| 2004/0034430 A1 * | 2/2004 | Falahee | 623/17.16 |
| 2004/0122518 A1 | 6/2004 | Rhoda | |
| 2004/0127993 A1 | 7/2004 | Kast et al. | |
| 2004/0133280 A1 * | 7/2004 | Trieu | 623/17.16 |
| 2004/0176853 A1 | 9/2004 | Sennett et al. | |
| 2005/0015149 A1 | 1/2005 | Michelson | |
| 2005/0021041 A1 | 1/2005 | Michelson | |
| 2005/0049704 A1 * | 3/2005 | Jackson | 623/17.11 |
| 2005/0070900 A1 | 3/2005 | Serhan et al. | |
| 2005/0119747 A1 * | 6/2005 | Monterumici et al. | 623/17.11 |
| 2006/0058878 A1 | 3/2006 | Michelson | |
| 2006/0149279 A1 | 7/2006 | Mathews | |
| 2006/0167547 A1 * | 7/2006 | Suddaby | 623/17.11 |
| 2006/0224241 A1 | 10/2006 | Butler et al. | 623/17.15 |
| 2006/0247771 A1 * | 11/2006 | Peterman et al. | 623/17.11 |
| 2007/0032872 A1 | 2/2007 | Simonton et al. | |
| 2007/0093897 A1 * | 4/2007 | Gerbec et al. | 623/17.11 |
| 2007/0162132 A1 | 7/2007 | Messerli | |
| 2007/0173938 A1 * | 7/2007 | Sweeney | 623/17.11 |
| 2007/0191951 A1 | 8/2007 | Branch, Jr. | |
| 2007/0233146 A1 * | 10/2007 | Henniges et al. | 606/91 |
| 2007/0260320 A1 | 11/2007 | Peterman et al. | |
| 2007/0276406 A1 | 11/2007 | Mahoney et al. | |
| 2007/0282441 A1 | 12/2007 | Stream et al. | |
| 2007/0293949 A1 | 12/2007 | Salerni et al. | |
| 2008/0009880 A1 | 1/2008 | Warnick et al. | |
| 2008/0015701 A1 | 1/2008 | Garcia et al. | |
| 2008/0071372 A1 | 3/2008 | Butler et al. | |
| 2008/0091211 A1 | 4/2008 | Gately | |
| 2008/0195209 A1 | 8/2008 | Garcia et al. | |
| 2008/0269756 A1 | 10/2008 | Tomko et al. | |
| 2008/0269901 A1 | 10/2008 | Baynham et al. | |
| 2008/0288076 A1 | 11/2008 | Soo et al. | |
| 2008/0306598 A1 | 12/2008 | Hansen et al. | |
| 2009/0043394 A1 | 2/2009 | Zdeblick et al. | |
| 2009/0177195 A1 | 7/2009 | Rawles et al. | |
| 2009/0204214 A1 | 8/2009 | Fuji et al. | |
| 2009/0228110 A1 | 9/2009 | McClintock | |
| 2009/0248163 A1 | 10/2009 | King et al. | |
| 2009/0248164 A1 | 10/2009 | Sweeney | |
| 2010/0004747 A1 | 1/2010 | Lin | |
| 2010/0016972 A1 | 1/2010 | Jansen et al. | |
| 2010/0023128 A1 | 1/2010 | Malberg | |
| 2010/0042218 A1 | 2/2010 | Nebosky et al. | |
| 2010/0063554 A1 | 3/2010 | Branch et al. | |
| 2010/0070041 A1 | 3/2010 | Peterman et al. | |

FOREIGN PATENT DOCUMENTS

| | | |
|---|---|---|
| JP | 2006187633 | 7/2006 |
| JP | 2007075632 | 3/2007 |
| JP | 2009207878 | 9/2009 |
| WO | WO 97306666 | 8/1997 |

* cited by examiner

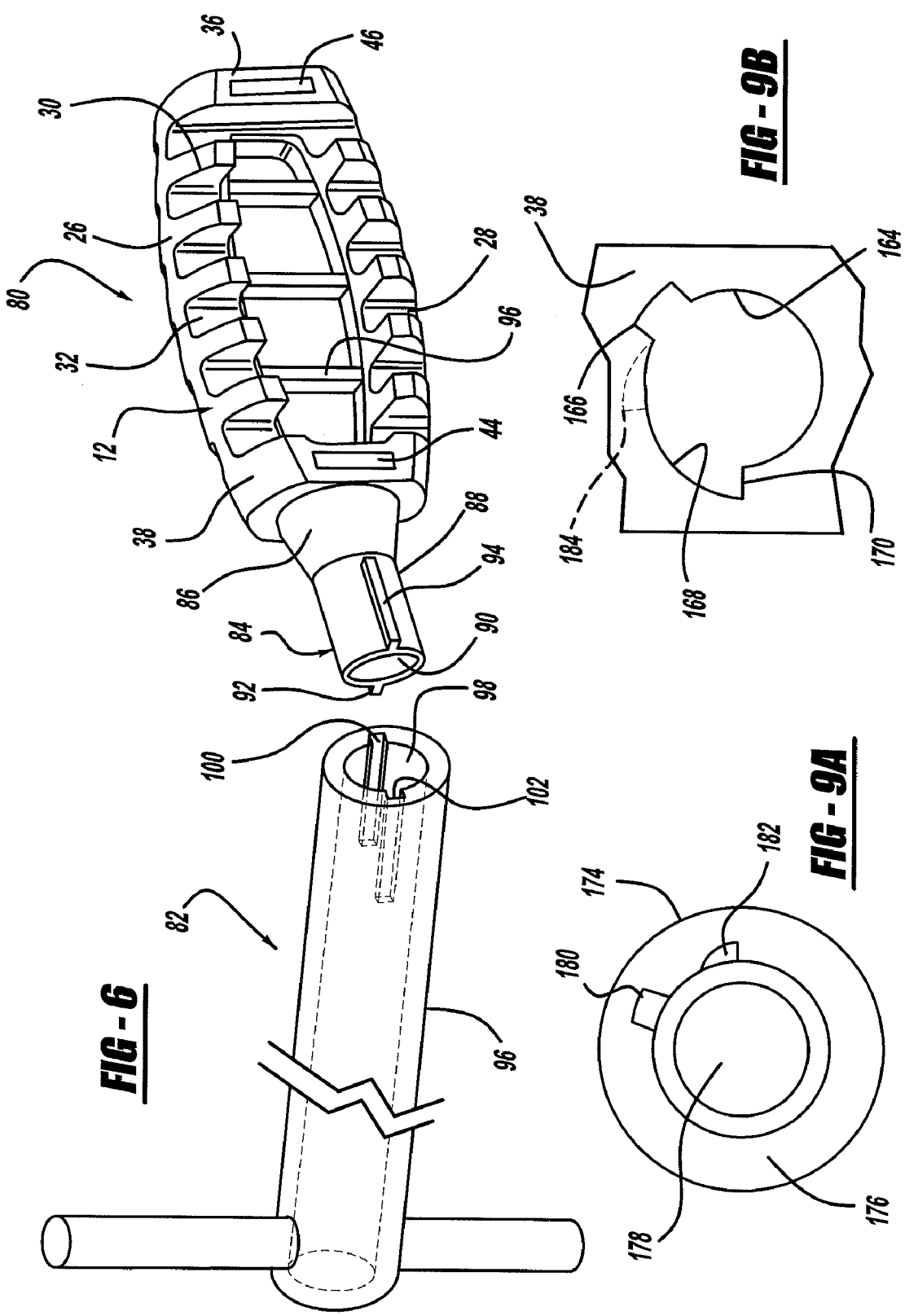

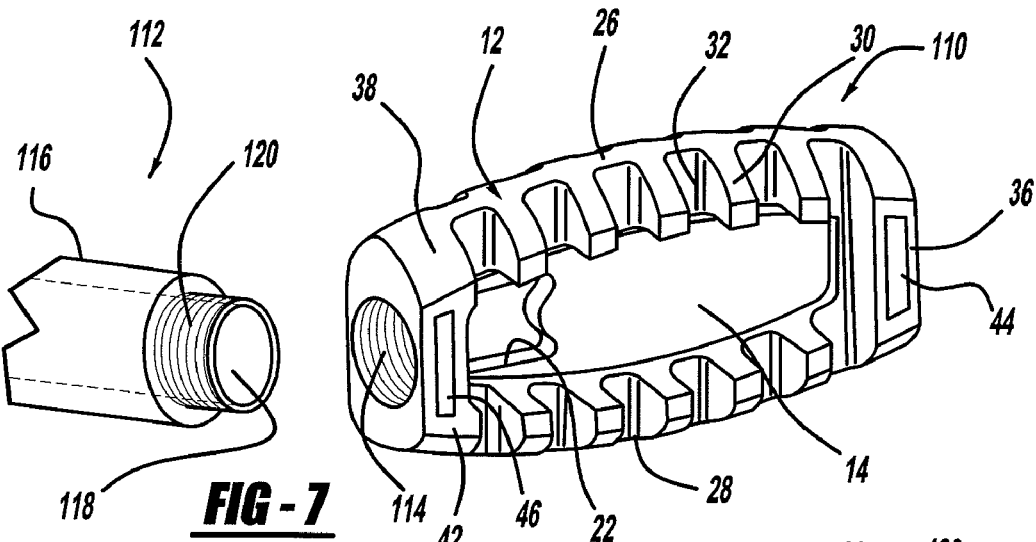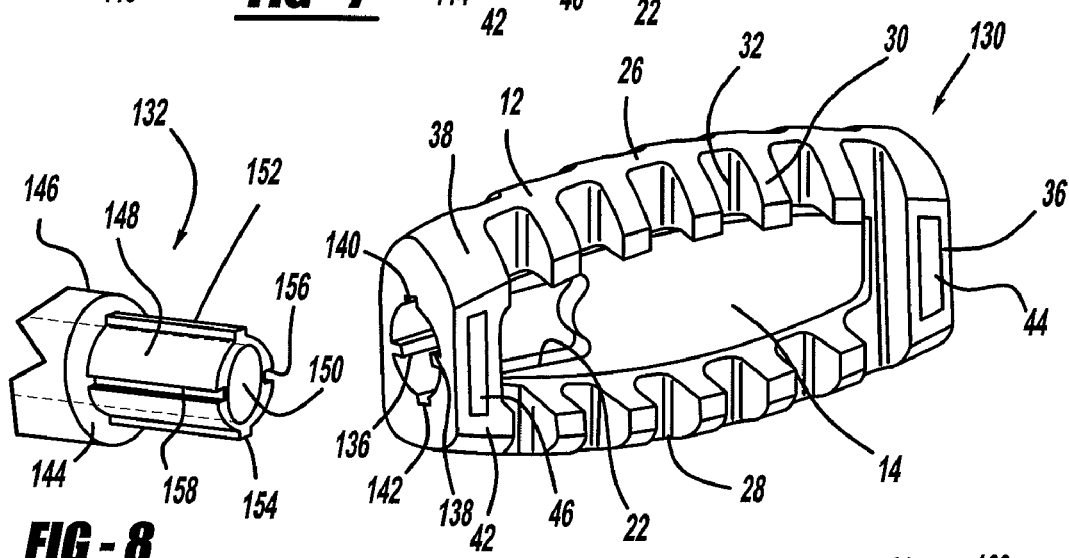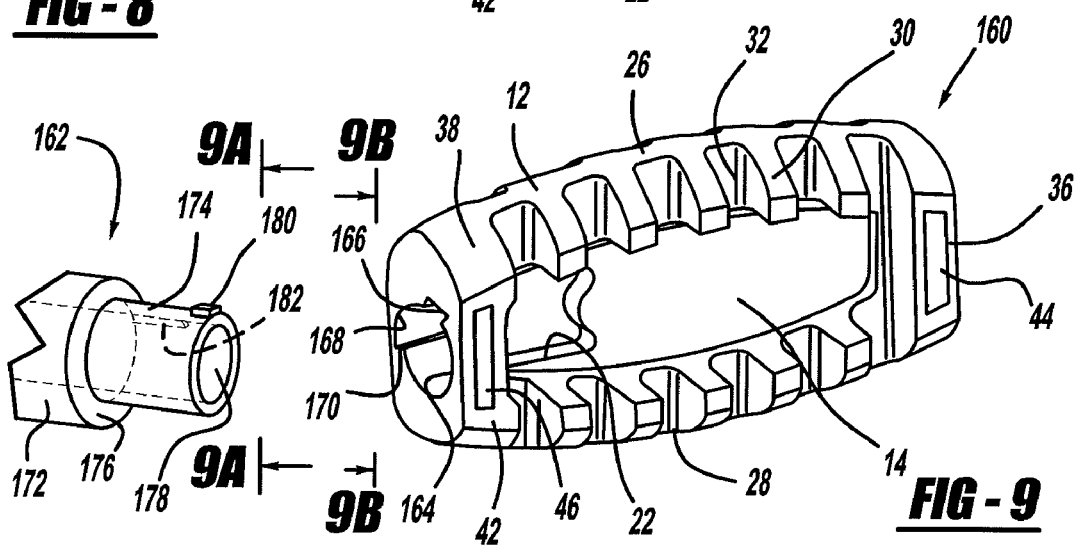

MINIMALLY INVASIVE INTERBODY DEVICE

BACKGROUND OF THE INVENTION

1. Field of the Invention

This invention relates generally to an interbody device for restoring the disc space height between two vertebrae during spinal fusion surgery and, more particularly, to an interbody device for restoring the disc space height between two vertebrae during minimally invasive spinal fusion surgery, where the device also allows for an effective distribution of bone graft material in the disc space.

2. Discussion of the Related Art

The human spine includes a series of vertebrae interconnected by connective tissue referred to as discs that act as a cushion between the vertebrae. The discs allow for movement of the vertebrae so that the back can bend and rotate.

Spinal fusion is a surgical procedure that fuses two or more vertebrae together using bone grafts and/or other devices. Spinal fusion is a commonly performed procedure for the treatment of chronic neck and back pain refractory to non-operative treatments. Spinal fusion is used to stabilize or eliminate motion of vertebrae segments that may be unstable, i.e., move in an abnormal way, that may lead to pain and discomfort. Spinal fusion is typically performed to treat injuries to the vertebrae, degeneration of the spinal discs, abnormal spinal curvature and a weak or unstable spine.

Spinal fusion generally requires a graft material, usually bone material, to fuse the vertebrae together. The bone graft material can be placed over the spine to fuse adjacent vertebrae together. Alternatively, a cage is positioned between the vertebrae being fused, and is filed with the bone graft material. The cage includes holes that allow the vertebrae and the graft material to grow together to provide the fusion. The cage supports the weight of adjacent vertebrae while the fusion is occurring through the holes in the cage.

Typically the bone graft material is autogenous bone material taken from the patient, or allograft bone material harvested from a cadaver. Synthetic bone material can also be used as the graft material. Generally, the patient's own bone material offers the best fusion material and is the current "gold standard." Known bone fusion materials include an iliac crest harvest from the patient, bone graft extenders, such as hydroxyapetite and demineralized bone matrix, and bone morphogenic protein.

In an attempt to preserve normal anatomical structures during spinal surgery, minimally invasive surgical procedures have been devised. One such procedure involves the use of a series of muscle dilators that separate the muscle fibers of the spine to create a pathway to the spine. A Kirschner (K-wire) is initially introduced through a small incision and directed towards the spinal pathology. The position of the K-wire is visualized by a fluoroscopic imaging system to identify its location. An initial narrow diameter muscle dilator is passed over the K-wire, and the K-wire is removed and subsequent larger muscle dilators are continually passed. When the opening is large enough, an access tube or retractor is positioned around the last muscle dilator through which the surgery is performed. The inner sequential muscle dilators are then removed allowing the surgeon to operate through the tubular retractor. The retractors come in a variety of lengths and diameters for different patients and procedures.

As mentioned above, a cage is typically positioned in the interbody region between the vertebrae after the disc has been removed. These cages typically have a box like design. The cage is forced into the interbody region through the surgical area where the bone and disc have been removed. The cage is filled with the bone graft material that subsequently fuses the vertebrae together. However, known cage designs are limited in that they only allow for partial filling of the interbody space where the graft material is maintained within the cage, thus only allowing partial fusion between the vertebrae. Further, the known bone graft cages are difficult to place because of their square or cylindrical shape, and put the nerve roots at risk during the procedure, sometimes resulting in injury. Also, the known cages do not allow the collapsed disc space height to be fully restored in that they cannot distract the open disc space once they are in place. Further, the known cage designs require that the bone graft material be placed in the cage prior to it being inserted into the interbody region, which limits the amount of bone material placed in the disc space and subsequent fusion surface. Also, once the cages are placed, they are difficult to remove and reposition.

SUMMARY OF THE INVENTION

In accordance with the teachings of the present invention, a minimally invasive interbody device is disclosed that restores the disc space height between two vertebrae and allows for the placement of bone graft material during spinal fusion surgery. The device includes a center plate surrounded by a perimeter portion that combine to have a relatively flat configuration in one dimension and relatively wide configuration in a perpendicular dimension. After the disc space has been cleared, the device is inserted into the disc space in a direction so that the wide dimension of the device is substantially parallel to the body of the vertebrae. The device is then rotated so that the wide dimension of the device becomes perpendicular to the vertebral body so as to cause the disc space height to be restored. Bone graft material is then introduced through a fill tube coupled to the device so that the bone graft material is distributed on both sides of the center plate around the perimeter portion and into the disc space, where the center plate helps to direct bone graft material around the device.

Additional features of the present invention will become apparent from the following description and appended claims, taken in conjunction with the accompanying drawings.

BRIEF DESCRIPTION OF THE DRAWINGS

FIG. 6 is a perspective view of a fill tube and a minimally invasive interbody device, according to another embodiment of the present invention;

FIG. 7 is broken-away perspective view of a fill tube and a minimally invasive interbody device employing a threaded attachment, according to another embodiment of the present invention;

FIG. 8 is a broken-away perspective view of a fill tube and a minimally invasive interbody device employing a tab and slot connection, according to another embodiment of the present invention;

FIG. 9 is a broken-away perspective view of a fill tube and a minimally invasive interbody device, according to another embodiment of the present invention;

FIG. 9A is an end view of the fill tube shown in FIG. 9;

FIG. 9B is a broken-away end view of the interbody device shown in FIG. 9;

FIG. 10 is a perspective view of a minimally invasive interbody device for restoring the disc space height during spinal fusion surgery, according to another embodiment of the present invention;

DETAILED DESCRIPTION OF THE EMBODIMENTS

The following discussion of the embodiments of the invention directed to a minimally invasive interbody device for restoring the disc space height during spinal fusion surgery and allowing dispersion of bone graft material within the disc space is merely exemplary in nature, and is in no way intended to limit the invention or its applications or uses.

Figure 1:
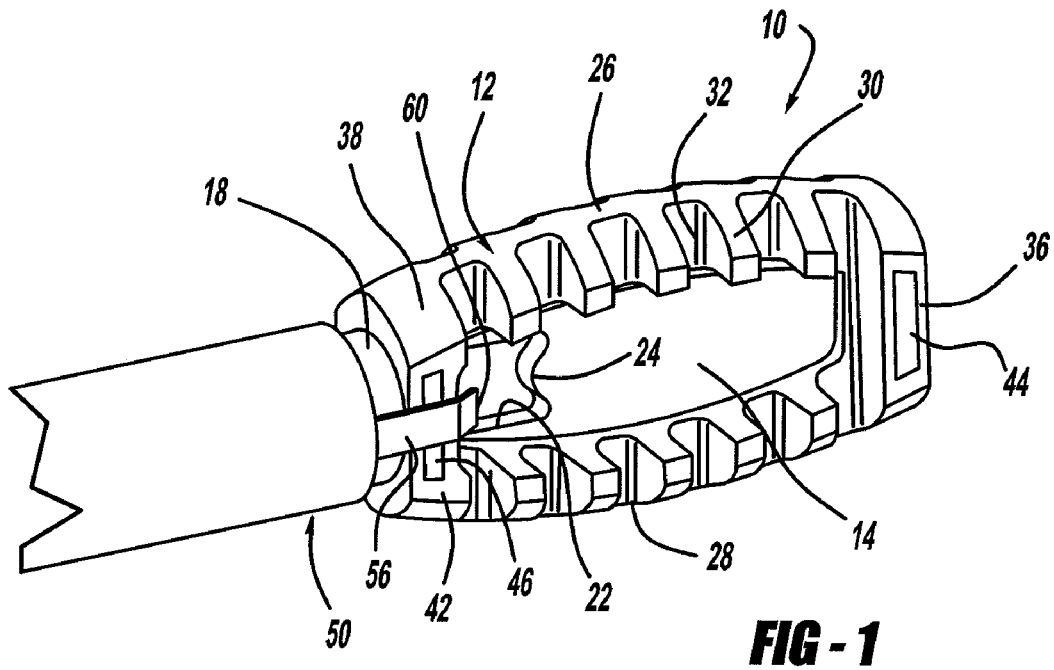
FIG. 1 is a perspective view of a minimally invasive interbody device for restoring the disc space height during spinal fusion surgery, according to an embodiment of the present invention.
Figure 2:
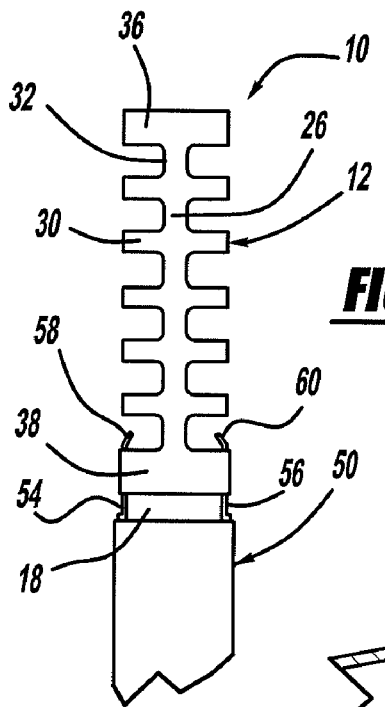
FIG. 2 is a top view of the interbody device shown in FIG. 1.
Figure 3:
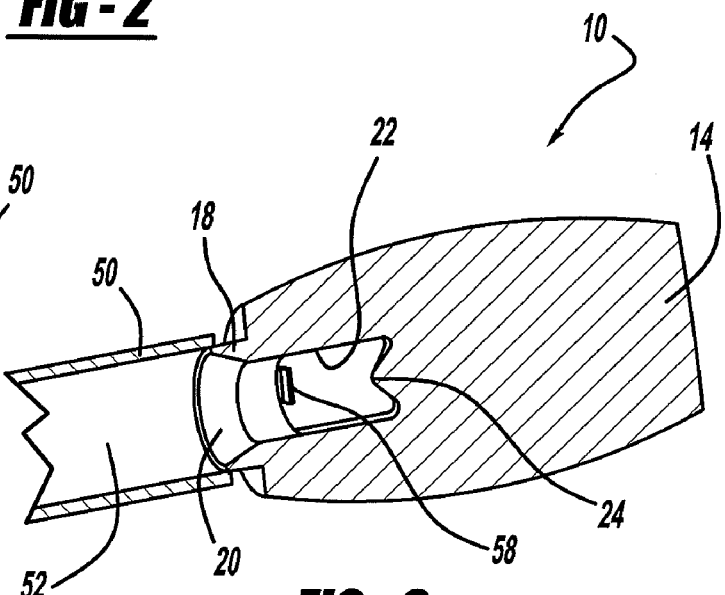
FIG. 3 is a cross-sectional, perspective view of the interbody device shown in FIG. 1.

FIG. 1 is a perspective view, FIG. 2 is a top view and FIG. 3 is a cross-sectional view of a minimally invasive interbody device 10 that is to be positioned within the interbody disc space between two vertebral bodies once the disc has been removed as part of a spinal fusion surgical procedure. As will be discussed in detail below, the device 10 operates to restore the disc space height that has been lost by age or damage and may be causing pain as a result of nerve pinching, as discussed above. Additionally, the device 10 facilitates the distribution of bone graft material within the disc space.

The interbody device 10 includes a perimeter portion 12 and a center plate 14 that are an integral body in this embodiment. The perimeter portion 12 includes opposing spines 26 and 28 having ribs 30 extending therefrom. The ribs 30 define spaces 32 between the ribs 30 along the length of the spines 26 and 28. The perimeter portion 12 also includes a first end piece 36 and a second end piece 38. A coupling tube 18 is formed to the end piece 38 where a bore 20 is defined through the coupling tube 18 and the end piece 38. The center plate 14 includes an opening 22 in communication with the bore 20 to facilitate the distribution of bone graft material. The center plate 14 includes a nub 24 extending into the opening 22, where the nub 24 helps to distribute the bone graft material on either side of the center plate 14 within the disc space. In an alternate embodiment, the center plate 14 can be eliminated. However, some load bearing structure may be needed between the spines 26 and 28.

Although this embodiment includes the spines 26 and 28 and the ribs 30, other embodiments can provide other configurations within the scope of the present invention. For example, the body of the device can be a solid piece having a consistent thickness, where an opening is provided in the body to distribute the bone graft material.

The device 10 can be made of any material suitable for the purposes described herein, such as titanium or a durable plastic. In one embodiment, the device 10 is radiolucent and is invisible on an X-ray. A reflective strip 44 can be attached to the end piece 36 and a reflective strip 46 can be attached to the end piece 38. The reflective strips 44 and 46 allow the ends of the device 10 to be visible on an X-ray so that the surgeon will know the position of the device 10 in the disc space.

As discussed above, the bone graft material is introduced through the coupling tube 18. In order to get the bone graft material to the coupling tube 18, a fill tube 50 is attached to the coupling tube 18, as shown. The fill tube 50 includes integral clasps 54 and 56 that extend from an end of the fill tube 50, as shown. The clasps 54 and 56 include angled end portions 58 and 60, respectively, that allow the clasps 54 and 56 to be mounted to the interbody device 10. The interbody device 10 is attached to the fill tube 50 outside of the patient. The fill tube 50 is an elongated member that extends out of the patient's body and allows the surgeon to position the interbody device 10 in the disc space, as will be discussed in more detail below. When the interbody device 10 is attached to the fill tube 50, the clasps 54 and 56 are spread apart and positioned within recesses 42 in the end piece 38, as shown. The clamping force of the clasps 54 and 56 allows the fill tube 50 to be securely attached to the device 10. Also, the angled end portions 58 and 60 are positioned against an opposite side of the end piece 38 to help lock the fill tube 50 the coupling tube 18. The clasps 54 and 56 are robust enough to allow the surgeon to rotate the fill tube 50, and cause the interbody device 10 to rotate within the disc space.

As discussed above, the bone graft material is inserted into the disc space through the coupling tube 18 and the end piece 38. In an alternate embodiment, the bone graft material can be inserted into the disc space through a port outside of the device 10, such as around the end piece 38.

Figure 4:
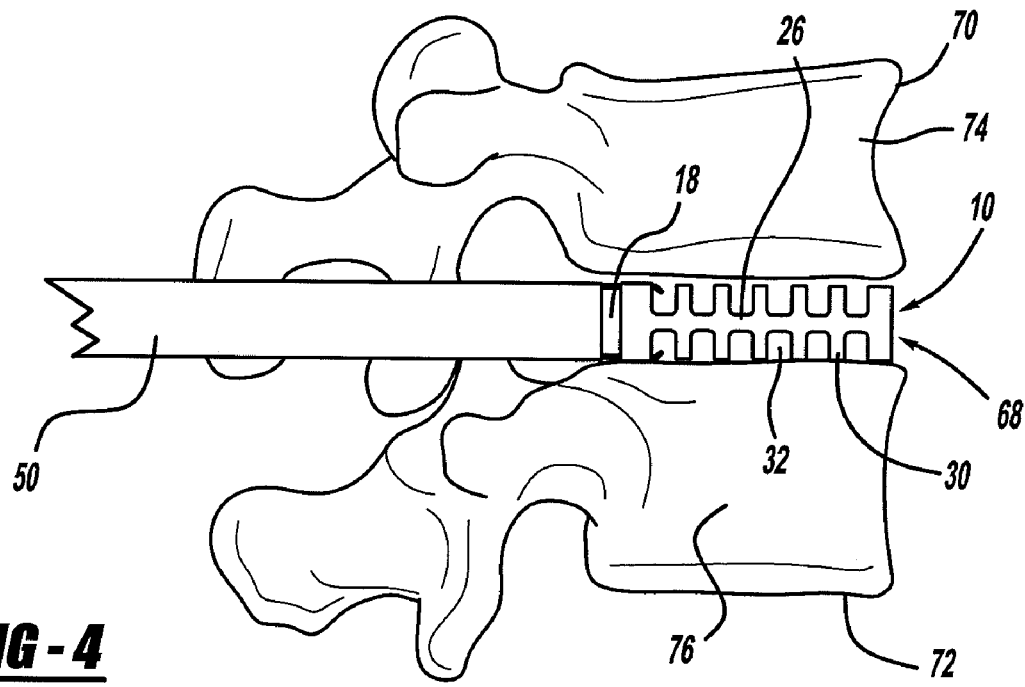
FIG. 4 is a side view of the interbody device shown in FIG. 1 positioned between two vertebrae in an insertion direction.
Figure 5:
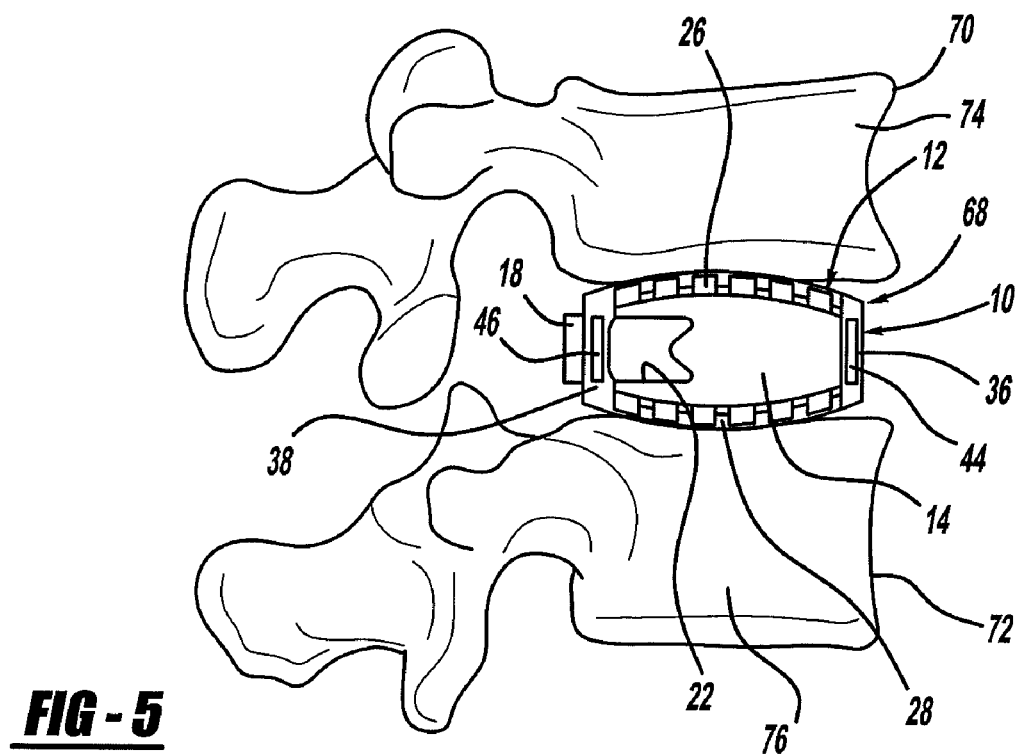
FIG. 5 is a side view of the interbody device shown in FIG. 1 positioned between the vertebrae in a disc height restoring direction.
Figure 1:
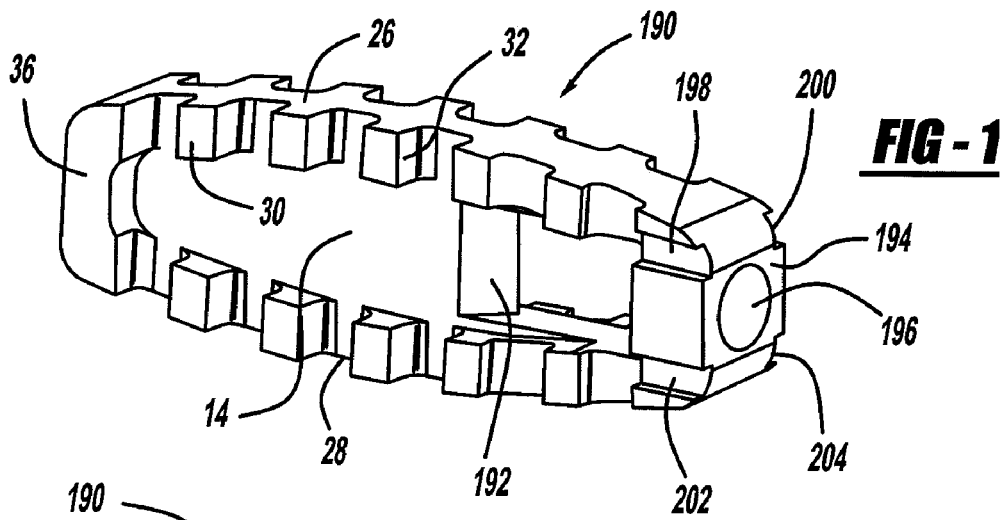

FIG. 4 shows the interbody device 10 positioned in a disc space 68 between two vertebrae 70 and 72 in an insertion direction where the wider dimension of the device 10 is parallel to the plane of vertebral bodies 74 and 76 of the vertebrae 70 and 72, respectively. Once the interbody device 10 is positioned within the disc space 68, as shown, the fill tube 50 is rotated so that the plane of the center plate 14 becomes perpendicular to the opposing faces of the vertebral bodies 74 and 76, as shown in FIG. 5.

Bone graft material is then introduced through the fill tube 50 into the interbody device 10 through the coupling tube 18 so that it flows into the opening 22 and is spread out on both sides of the center plate 14. The bone graft material will enter the spaces 32 between the ribs 30, and provide a complete and even distribution of bone graft material within the disc space 68 for proper vertebral fusion.

Once the bone graft material has been forced into the disc space, the fill tube 50 is pulled off of the interbody device 10. The clasping strength of the clasps 54 and 56 allow the interbody device 10 to be held to the fill tube 50, but also be removed therefrom under a reasonably low enough force. The interbody device 10 remains in the disc space 68 to maintain the disc space height and facilitate bone fusion.

The spines 26 and 28 and the ribs 30 define the width of the device 10 and the distance between the ribs 26 and 28 defines the height of the device 10. The height of the interbody device 10 is selected to be the desired disc height for a particular disc space so that the disc height is restored by the device 10 as part of the fusion process. The interbody device 10 can be provided in different lengths and heights to accommodate the anatomy of different patients. The width of the device 10 is such that it can be relatively easily slipped into the disc space 68 through a dilator tube (not shown) used in minimally invasive surgical procedures without risk of injury to the nerve roots through the same channel that the disc has been removed from. In one non-limiting embodiment, the device 10 has a width in the range of 3-4 mm and a height in the range of 8-15 mm. The length of the device 10 would be suitable for the size of the disc space, such as 15-25 mm.

FIG. 6 is a broken-away perspective view of a minimally invasive interbody device 80 and associated fill tube handle 82, according to another embodiment of the present invention, where like elements to the device 10 are identified by the same reference numeral. In this embodiment, the coupling tube 18 is replaced with a coupling tube 84. The coupling tube 84 has a tapered portion 86 and a cylindrical portion 88, both having a bore 90 running therethrough. Two elongated opposing tabs 92 and 94 are formed to an outside surface of the cylindrical portion 88. The center plate 14 has been replaced with a series of support columns 96 to provide support when the interbody device 80 is rotated within the disc space. The support columns 96 are intended to represent any suitable load bearing structure within the space defined by the perimeter portion 12

The fill tube handle 82 includes a fill tube 96 having a central bore 98. A pair of slots 100 and 102 is formed in the bore 98 in alignment with the elongated tabs 92 and 94. The fill tube handle 82 is slipped on to the coupling portion 84 so that the tabs 92 and 94 slide down the slots 100 and 102. The internal bore 98 then forced onto the tapered portion 86 to lock the handle 82 to the interbody device 80. The coupling between the tabs 92 and 94 and the slots 100 and 102 is robust enough so that the interbody device 80 can be rotated within the disc space. Although two of the tabs 92 and 94 are used in this embodiment, it will be appreciated by those skilled in the art that a single tab and slot configuration may be adequate, or more than two tab and slot couplings may be needed. The cylindrical portion 88 is positioned within the bore 98 so that minimal resistance is provided for depositing bone graft material down the bore 98, through the coupling portion 84 and into the space between the ribs 26 and 28.

FIG. 7 is a perspective view of a minimally invasive interbody device 110 and associated fill tube 112, according to another embodiment of the present invention, where like elements to the interbody device 10 are identified by the same reference numeral. In this embodiment, the coupling tube 18 is replaced with a threaded bore 114 that extends through the end piece 38. The fill tube 112 includes a fill tube body 116 having a bore 118 and a threaded end portion 120 at the end of the body 116. The threaded end portion 120 is threaded into the threaded portion 114 in the proper direction to attach and detach the fill tube 112 to the device 110 so that the fill tube 112 can rotate the interbody device 110.

FIG. 8 is a perspective view of a minimally invasive interbody device 130 and associated fill tube 132, according to another embodiment of the present invention, where like elements to the interbody device 10 are identified by the same reference numeral. In this embodiment, the coupling tube 18 is replaced with an internal bore 134 that includes elongated tabs 136 and 138 and slots 140 and 142. The fill tube 132 includes a fill tube body 146 and a narrow diameter end portion 148 defining a shoulder 144 therebetween, where a central bore 150 extends through the fill tube body 146 and the end portion 148. The end portion 148 includes tabs 152 and 154 and slots 156 and 158 that align with the tabs 136 and 138 and the slots 140 and 142 in the bore 134 so as to allow the device 130 to be rotated by the fill tube 132 when the end portion 148 is inserted into the bore 134. Although a specific configuration of tabs and slots are shown between the end portion 148 and the bore 134, any suitable configuration of tab and slots in this manner can be used within the scope of the present invention. The device 130 is held to the fill tube 132 by a friction engagement between the end portion 148 and the bore 134. Alternately, the end portion 148 and the bore 134 can be tapered as a wider diameter to a narrower diameter to provide a better locking arrangement. The shoulder 144 prevents the fill tube 132 from being pushed into the device 130.

FIG. 9 is a perspective view of a minimally invasive interbody device 160 and associated fill tube 162, according to another embodiment of the present invention, where like elements to the device 10 are identified by the same reference numeral. FIG. 9A is an end view of the fill tube 162 and FIG. 9B is a broken-away end view of the device 160. In this embodiment, the coupling tube 18 is replaced with an internal bore 164 that includes a slot 166 and an arced portion 168 defining the ledge 170. The fill tube 162 includes a fill tube body 172 and a narrow diameter end portion 174 defining a shoulder 176 therebetween, where a central bore 178 extends through the fill tube body 162 and the end portion 174. A nub 180 is attached to the end of the end portion 174 and a stop 182 is attached to the end portion 174, as shown. The end portion 174 is inserted into the bore 164 so that the nub 180 aligns with the slot 166. The end portion 174 is slid into the bore 164 so that the nub 180 extends behind the end piece 38. The fill tube 162 is rotated so the nub 180 locks behind the end piece 38. At the same time, the nub 180 rides up a ramp 184 so that the stop 182 is rotated and contacts the ledge 170. The contact between the stop 182 and the ledge 170 allows the device 160 to be rotated within the disc space, as discussed above. The shoulder 176 and the nub 180 lock the fill tube 162 to the device 160. The fill tube 162 can then be rotated in the opposite direction so that the nub 180 again aligns with the slot 166 to remove the fill tube 162, as discussed above.

FIG. 10 is a perspective view of a minimally invasive interbody device 190 for restoring the disc space height during spinal fusion surgery, according to an embodiment of the present invention, where like elements to the device 10 are identified by the same reference numeral. In this embodiment, the nub 24 is replaced with a triangular ridge 192 that distributes the bone graft material on both sides of the center plate 14. Further, the end piece 38 is replaced with an end piece 194. The end piece 194 includes a cylindrical bore 196 extending therethrough. The end piece 194 also includes a first set of two opposing slots 198 and 200 on opposite sides of the end piece 194 and a second set of two opposing slots 202 and 204 on opposite sides of the end piece 194, as shown.

Figure 11:
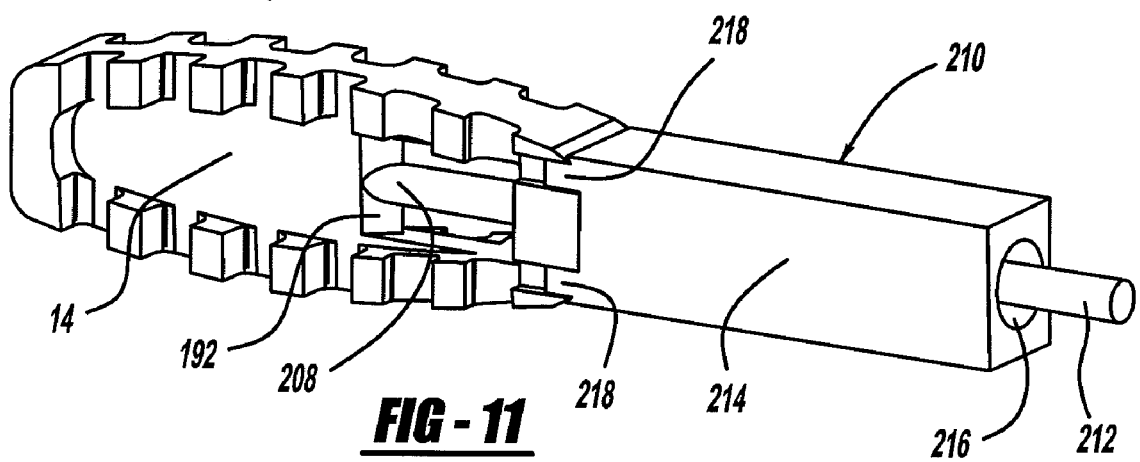
FIG. 11 is a perspective view of the minimally invasive interbody device shown in FIG. 10 and including a rotating tool and a fill tube.

FIG. 11 is a perspective view of the interbody device 190 in combination with a rotating tool 210 and a fill tube 212. The rotating tool 210 includes a rectangular body 214 having a cylindrical bore 216 extending therethrough. The body 214 includes four rigid fingers 218 that are configured to be positioned within the slots 198-204, as shown, to allow the tool 210 to rotate the interbody device 190 for the purposes discussed above. The fill tube 212 extends through the bore 216 and is coupled to or positioned relative to the ridge 190 so that bone graft material forced through the tube 212 is dispersed on both sides of the center plate 14 as discussed above. The end 208 of the fill tube 212 may have a shape that conforms with the shape of the ridge 192.

Figure 12:
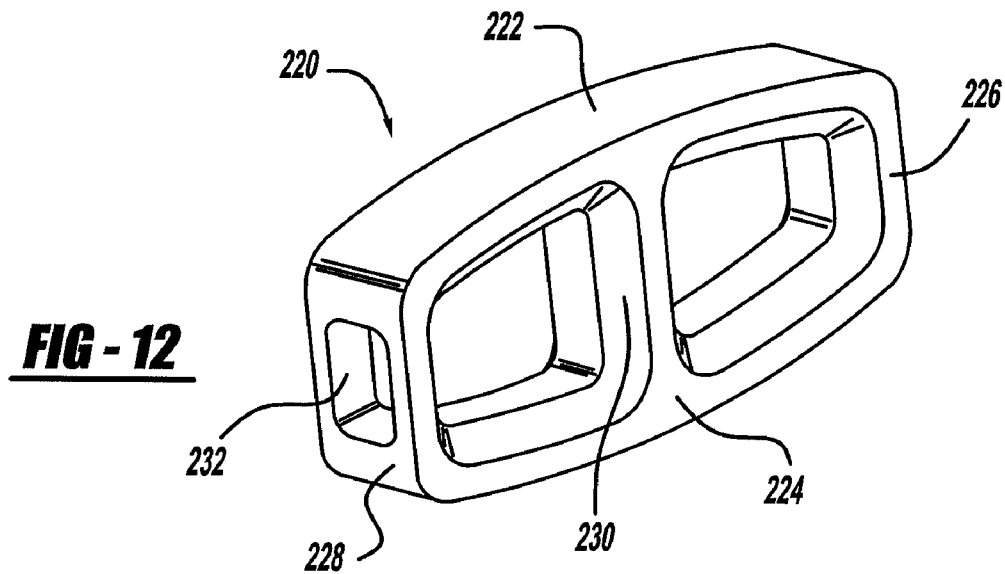
FIG. 12 is a perspective view of a minimally invasive interbody device for restoring the disc space height during spinal fusion surgery, according to an embodiment of the present invention.

FIG. 12 is a perspective view of a minimally invasive interbody device 220 for restoring the disc space height during spinal fusion surgery, according to an embodiment of the present invention. The device 220 includes opposing elongated members 222 and 224 and opposing end pieces 226 and 228 that combine to define a perimeter structure. A center member 230 is coupled to the elongated members 222 and 224 and provides structural support. A rectangular opening 232 is provided through the end piece 228, and accepts a fill tube and rotating tool to rotate the interbody device 220 and provide the bone graft material within the perimeter structure, as discussed above.

The foregoing discussion discloses and describes merely exemplary embodiments of the present invention. One skilled in the art will readily recognize from such discussion and from the accompanying drawings and claims that various changes, modifications and variations can be made therein without departing from the spirit and scope of the invention as defined in the following claims.

What is claimed is:

1. An interbody device for restoring the disc space height of the disc space between opposing vertebral bodies of adjacent vertebrae during a spinal fusion procedure, said device comprising:
   a perimeter portion including spaced apart elongated members extending along a length of the perimeter portion and opposing end pieces coupled to the elongated members, wherein one of the end pieces includes a channel extending therethrough; and
   a center plate member positioned within the perimeter portion and extending along the length of the perimeter portion, said center plate member extending along a central plane of the device between the end pieces of the device, said plate member including an opening proximate the channel so that a bonegraft material introduced through the channel and into the opening is distributed by the plate member to both sides of the plate member and the perimeter portion, wherein the device has a length defined by the distance between the end pieces, a width defined by the width of the elongated members and a height defined by the distance between the elongated members where the height of the device is substantially greater than the width of the device so that the device is operable to be inserted into the disc space in a substantially flat orientation and be rotated to an orientation where the elongated members contact the opposing vertebral bodies, wherein the plate member includes a nub that extends into the opening.

2. The interbody device of claim 1, wherein the device is radiolucent.

3. The interbody device of claim 1, wherein the end pieces include reflective strips that are visible on an X-ray.

4. An interbody device for restoring the disc space height of the disc space between opposing vertebral bodies of adjacent vertebrae during a spinal fusion procedure, said device comprising:
   a perimeter portion including spaced apart elongated members extending along a length of the perimeter portion and opposing end pieces coupled to the elongated members, wherein one of the end pieces includes a channel extending therethrough; and
   a center plate member positioned within the perimeter portion and extending along the length of the perimeter portion, said center plate member extending along a central plane of the device between the end pieces of the device, said plate member including an opening proximate the channel so that a bonegraft material introduced through the channel and into the opening is distributed by the plate member to both sides of the plate member and the perimeter portion, wherein the device has a length defined by the distance between the end pieces, a width defined by the width of the elongated members and a height defined by the distance between the elongated members where the height of the device is substantially greater than the width of the device so that the device is operable to be inserted into the disc space in a substantially flat orientation and be rotated to an orientation where the elongated members contact the opposing vertebral bodies, wherein the plate member includes a triangular ridge that extends into the opening.

5. The interbody device of claim 4, wherein the device is radiolucent.

6. The interbody device of claim 4, wherein the end pieces include reflective strips that are visible on an X-ray.

7. An interbody device for restoring the disc space height of the disc space between opposing vertebral bodies of adjacent vertebrae during a spinal fusion procedure, said device comprising:
   a perimeter portion including spaced apart elongated members extending along a length of the perimeter portion and opposing elongated members, wherein one of the end pieces includes a channel extending therethrough; and
   a center plate member positioned within the perimeter portion and extending along the length of the perimeter portion, said center plate member extending along a central plane of the device between the end pieces of the device, said plate member including an opening proximate the channel so that a bonegraft material introduced through the channel and into the opening is distributed by the plate member to both sides of the plate member and the perimeter portion, wherein the device has a length defined by the distance between the end pieces, a width defined by the width of the elongated members and a height defined by the distance between the elongated members where the height of the device is substantially greater than the width of the device so that the device is operable to be inserted into the disc space in a substantially flat orientation and be rotated to an orientation where the elongated members contact the opposing vertebral bodies, wherein the device is radiolucent.

8. An interbody device for restoring the disc space height of the disc space between opposing vertebral bodies of adjacent vertebrae during a spinal fusion procedure, said device comprising:
   a perimeter portion including spaced apart elongated members extending along a length of the perimeter portion and opposing end pieces coupled to the elongated members, wherein one of the end pieces includes a channel extending therethrough; and
   a center plate member positioned within the perimeter portion and extending along the length of the perimeter portion, said center plate member extending along a central plane of the device between the end pieces of the device, said plate member including an opening proximate the channel so that a bonegraft material introduced through the channel and into the opening is distributed by the plate member to both sides of the plate member and the perimeter portion, wherein the device has a length defined by the distance between the end pieces, a width defined by the width of the elongated members and a height defined by the distance between the elongated members where the height of the device is substantially greater than the width of the device so that the device is operable to be inserted into the disc space in a substantially flat orientation and be rotated to an orientation where the elongated members contact the opposing vertebral bodies, wherein the end pieces include reflective strips that are visible on an X-ray.

9. An interbody device for restoring the disc space height of the disc space between opposing vertebral bodies of adjacent vertebrae during a spinal fusion procedure, said device comprising:

a perimeter portion including spaced apart elongated members extending along a length of the perimeter portion and opposing end pieces coupled to the elongated members, wherein one of the end pieces includes a channel extending therethrough; and a center plate member positioned within the perimeter portion and extending along the length of the perimeter portion, said center plate member extending along a central plane of the device between the end pieces of the device, said plate member including an opening proximate the channel so that a bonegraft material introduced through the channel and into the opening is distributed by the plate member to both sides of the plate member and the perimeter portion, wherein the device has a length defined by the distance between the end pieces, a width defined by the width of the elongated members and a height defined by the distance between the elongated members where the height of the device is substantially greater than the width of the device so that the device is operable to be inserted into the disc space in a substantially flat orientation and be rotated to an orientation where the elongated members contact the opposing vertebral bodies, wherein the channel extending through the end piece is configured to accept a fill tube that is operable to rotate the device and distribute a bone graft material through the channel and into the device, wherein the fill tube has a rectangular shape and includes a plurality of fingers that are positioned within slots in an outside surface of the one end piece.

10. An interbody device for restoring the disc space height of the disc space between opposing vertebral bodies of adjacent vertebrae during a spinal fusion procedure, said device comprising:

a perimeter portion including spaced apart elongated members extending along a length of the perimeter portion and opposing end pieces coupled to the elongated members, wherein one of the end pieces includes a channel extending therethrough; and a center plate member positioned within the perimeter portion and extending along the length of the perimeter portion, said center plate member extending along a central plane of the device between the end pieces of the device, said plate member including an opening proximate the channel so that a bone aft material introduced through the channel and into the opening is distributed by the plate member to both sides of the plate member and the perimeter portion, wherein the device has a length defined by the distance between the end pieces, a width defined by the width of the elongated members and a height defined by the distance between the elongated members where the height of the device is substantially greater than the width of the device so that the device is operable to be inserted into the disc space in a substantially flat orientation and be rotated to an orientation where the elongated members contact the opposing vertebral bodies, wherein the channel extending through the end piece is configured to accept a fill tube that is operable to rotate the device and distribute a bone graft material through the channel and into the device, wherein the channel includes a slot and an arced cut-out portion and the fill tube includes a nub and a ramp, wherein the slot, cut-out portion, nub and ramp are configured to engage each other to allow the interbody device to be rotated.

11. An interbody device assembly for restoring the disc space height of the disc space between two vertebral bodies of adjacent vertebra during a spinal fusion procedure, said assembly comprising:

an interbody device including a perimeter portion having spaced apart spines extending along a length of the perimeter portion and opposing end pieces coupled to the spines, wherein one of the end pieces includes a channel extending therethrough, and wherein the perimeter portion has a length defined by the distance between the end pieces, a width defined by the width of the spines and a height defined by the distance between the spines where the height of the device is substantially greater than the width of the device, said interbody device further including a center plate positioned within the perimeter portion and including an opening proximate the channel, said center plate extending along the length of the perimeter portion, said center plate extending along a central plane of the device between the end pieces of the device, wherein the device is operable to be inserted between two vertebrae in a disc space and then rotated to restore disc space height; and a fill tube coupled to the one end piece and in fluid communication with the channel, wherein the fill tube is operable to provide bone graft material to the space within the perimeter portion and the center plate is effective to distribute the bone graft material within the disc space on both sides of the device, said fill tube also being operable to rotate the interbody device, wherein the channel includes one or more of a slot and an elongated tab and the fill tube includes one or more of a slot and an elongated tab that are configured to engage each other to allow the perimeter portion to be rotated.

12. The interbody device assembly of claim 11, wherein the center plate includes a nub that extends into the opening.

13. The interbody device assembly of claim 11, wherein the center plate includes a triangular ridge that extends into the opening.

14. An interbody assembly comprising an interbody device to be positioned within a disc space between two vertebrae, said device including an opening and a center plate extending along the length of the device, said center plate extending along a central plane of the device between ends of the device, said assembly further comprising a fill tube including a fill chamber, said fill tube being coupled to the device so that bone graft material can be passed through the fill chamber in the fill tube and into the opening in the device and being distributed within the disc space on both sides of device by the center plate, said fill tube also being operable to rotate the device, wherein the center plate includes a nub that extends into the opening and operates to effectively distribute the bone graft material.

15. An interbody assembly comprising an interbody device to be positioned within a disc space between two vertebrae, said device including an opening and a center plate extending along the length of the device, said center plate extending along a central plane of the device between ends of the device, said assembly further comprising a fill tube including a fill chamber, said fill tube being coupled to the device so that bone graft material can be passed through the fill chamber in the fill tube and into the opening in the device and being distributed within the disc space on both sides of device by the center plate, said fill tube also being operable to rotate the device, wherein the center plate includes a triangular ridge that extends into the opening and operates to effectively distribute the bone graft material.

* * * * *